United States Patent [19]
Bennett et al.

[11] Patent Number: 5,929,303
[45] Date of Patent: Jul. 27, 1999

[54] FRUIT-SPECIFIC AND RIPENING-REGULATION EXPANSIN GENES TO CONTROL FRUIT TEXTURE AND SOFTENING

[75] Inventors: Alan B. Bennett; Jocelyn K. C. Rose, both of Davis, Calif.

[73] Assignee: The Regents of the University of California, Oakland, Calif.

[21] Appl. No.: 08/845,539

[22] Filed: Apr. 25, 1997

[51] Int. Cl.$^6$ .............................. A01H 5/00; A01H 5/08; C12N 15/29; C12N 15/82

[52] U.S. Cl. .................. 800/284; 800/263; 800/286; 800/287; 800/290; 800/298; 800/307; 800/308; 800/309; 800/310; 800/317.4; 435/69.1; 435/468; 536/23.6; 536/24.5

[58] Field of Search .......................... 435/172.3, 320.1, 435/468, 69.1; 536/23.6, 24.5; 800/205, DIG. 18, DIG. 37, DIG. 44, 263, 284, 286, 287, 290, 298, 307–310, 317.4

[56] References Cited

U.S. PATENT DOCUMENTS

| | | | |
|---|---|---|---|
| 5,034,323 | 7/1991 | Jorgensen et al. | 435/172.3 |
| 5,231,020 | 7/1993 | Jorgensen et al. | 435/172.3 |
| 5,283,184 | 2/1994 | Jorgensen et al. | 435/172.3 |
| 5,365,015 | 11/1994 | Grierson et al. | 800/205 |
| 5,569,931 | 10/1996 | DellaPenna | 800/205 |

FOREIGN PATENT DOCUMENTS

| | | | |
|---|---|---|---|
| A-40262/95 | 4/1996 | Australia | C12N 9/00 |

OTHER PUBLICATIONS

Cosgrove, D.J., *BioEssays* 18:533 (1996).
DellaPenna, D., et al., *Plant Physiol.* 85:502 (1987).
DellaPenna, D., et al., *Proc. Natl. Acad. Sci. USA* 83:6420 (1986).
Lanahan, M.B., et al., *Plant Cell* 6:521 (1994).
McQueen–Mason, S.J., et al., *Plant Cell* 4:1425 (1992).
McQueen–Mason, S.J., et al., *Planta* 190:327 (1993).
McQueen–Mason, S.J. and Cosgrove, D.J. *Plant Physiol.* 107:87 (1995).
Meier, et al., *Plant Cell* 3:309–316 (1991).
Mitcham, E.J., et al., *Phytochem.*30:1777 (1978).
Oeller, P.W., et al., *Science* 254:437 (1991).
Rose, J.K.C., et al, *Plant Physiol.* 110:493 (1996).
Shcherban, T.Y., et al., *Proc. Natl. Acad. Sci. USA* 92:9245 (1995).
Theologis, A., *Cell* 70:181 (1992).
Tigchelaar, E.C., et al., *HortScience* 13:508 (1978).
Wilkinson, J.O., et al., *Science* 270:1807 (1995).
Shcherban et al. Molecular cloning and sequence analysis of expansins—a highly conserved, multigene family of proteins that mediate cell wall extension in plants. PNAS USA. 92:9245–9249, Sep. 1995.
Smith et al. Antisense RNA inhibition of polygalacturonase gene expression gene expression in transgenic tomatoes. Nature. 334:724–726, Aug. 1988.
Nehra et al. Genetic transformation of strawberry by *Agrobacterium tumefaciens* using a leaf disk regeneration system. Plant Cell Reports. 9:293–298, Sep. 1990.
Chee. Transformation of *Cucumis sativus* tissue by *Agrobacterium tumefaciens* and the regeneration of transformed plants. Plant Cell Reports. 9:245–248, Sep. 1990.
Napoli et al. Introduction of a chimeric chalcone synthase gene into petunia results in reversible co–suppression of homologous genes in trans. The Plant Cell. 2:279–289, Apr. 1990.
Hyung–Taeg Cho, et al., "Expression of Expansin Genes is Correlated with Growth in Deepwater Rice," *The Plant Cell* 9:1661–1671 (Sep. 1997).

*Primary Examiner*—David T. Fox
*Attorney, Agent, or Firm*—Townsend and Townsend Crew LLP

[57] ABSTRACT

Expansins are proteins that induce extension in isolated plant cell walls in vitro and have been proposed to disrupt non-covalent interactions between hemicellulose and cellulose microfibrils. Because the plant primary cell wall acts as a constraint to cell enlargement, this process may be integral to plant cell expansion and studies of expansins have focused on their role in growth. We have discovered an expansin (Ex1) from tomato, melon and strawberry that is highly abundant and specifically expressed in ripening fruit, a developmental period when growth has ceased but when selective disassembly of cell wall components is pronounced. Also disclosed are expression vectors containing the Ex1 coding sequence, expression vectors containing an Ex1 sequence in the antisense orientation, Ex1 proteins, and transgenic plants which express both sense and antisense exogenous Ex1.

30 Claims, 2 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 28..702
        (D) OTHER INFORMATION: /product= "tomato LeEx1"

(xi) SEQUENCE DESCRIPTION: SEQ ID NO:1:

```
GAACTTCAAT TCCATTAAAT CTTAAGA ATG GGT ATC ATA ATT TTC ATC CTT         51
                            Met Gly Ile Ile Ile Phe Ile Leu
                             1               5

GTT CTT CTT TTT GTA GAC TCA TGT TTC AAC ATT GTT GAA GGA AGA ATC        99
Val Leu Leu Phe Val Asp Ser Cys Phe Asn Ile Val Glu Gly Arg Ile
     10                  15                  20

CCT GGT GTT TAC TCT GGT GGT TCA TGG GAA ACT GCA CAT GCT ACA TTT       147
Pro Gly Val Tyr Ser Gly Gly Ser Trp Glu Thr Ala His Ala Thr Phe
 25                  30                  35                  40

TAC GGC GGA AGT GAT GCT TCT GGA ACA ATG GGC GGT GCG TGT GGT TAT       195
Tyr Gly Gly Ser Asp Ala Ser Gly Thr Met Gly Gly Ala Cys Gly Tyr
                 45                  50                  55

GGA AAT TTA TAC AGC CAA GGA TAC GGA GTT AAC ACA GCA GCA CTG AGT       243
Gly Asn Leu Tyr Ser Gln Gly Tyr Gly Val Asn Thr Ala Ala Leu Ser
             60                  65                  70

ACT GCT TTG TTT AAC AAT GGA TTA AGT TGT GGA GCC TGT TTT GAA CTT       291
Thr Ala Leu Phe Asn Asn Gly Leu Ser Cys Gly Ala Cys Phe Glu Leu
         75                  80                  85
```

```
AAA TGT ACA AAT ACT CCT AAT TGG AAA TGG TGT CTT CCT GGA AAC CCT       339
Lys Cys Thr Asn Thr Pro Asn Trp Lys Trp Cys Leu Pro Gly Asn Pro
        90                  95                 100

TCC ATT TTA ATC ACA GCT ACC AAT TTC TGC CCA CCA AAT TAC GCG TTG       387
Ser Ile Leu Ile Thr Ala Thr Asn Phe Cys Pro Pro Asn Tyr Ala Leu
105             110                 115                 120

CCA AAT GAC AAT GGT GGC TGG TGT AAC CCT CCT CGC CCT CAC TTT GAC       435
Pro Asn Asp Asn Gly Gly Trp Cys Asn Pro Pro Arg Pro His Phe Asp
                125                 130                 135

CTC GCT ATG CCT ATG TTT CTC AAA CTT GCT CAG TAC CGC GCT GGC ATT       483
Leu Ala Met Pro Met Phe Leu Lys Leu Ala Gln Tyr Arg Ala Gly Ile
            140                 145                 150

GTT CCT GTA ACT TAT CGC AGG ATC CCA TGC CGA AAG CAA GGA GGA ATC       531
Val Pro Val Thr Tyr Arg Arg Ile Pro Cys Arg Lys Gln Gly Gly Ile
                155                 160                 165

AGA TTT ACC ATC AAT GGA TTC CGT TAC TTC AAC TTA GTG TTG ATC ACG       579
Arg Phe Thr Ile Asn Gly Phe Arg Tyr Phe Asn Leu Val Leu Ile Thr
        170                 175                 180

AAT GTA GCA GGT GCA GGG GAT ATT ATT AAG GTT TGG GTA AAA GGA ACA       627
Asn Val Ala Gly Ala Gly Asp Ile Ile Lys Val Trp Val Lys Gly Thr
185             190                 195                 200

AAG ACA AAT TGG ATT CCA TTG AGC CGT AAT TGG GGA CAA AAT TGG CAA       675
Lys Thr Asn Trp Ile Pro Leu Ser Arg Asn Trp Gly Gln Asn Trp Gln
                205                 210                 215

TCA AAT GCG GTT TTA ACT GGT CAA TCA                                   702
Ser Asn Ala Val Leu Thr Gly Gln Ser
                220                 225

(2) INFORMATION FOR SEQ ID NO:2:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Ile Ile Ile Phe Ile Leu Val Leu Leu Phe Val Asp Ser Cys
 1               5                  10                  15

Phe Asn Ile Val Glu Gly Arg Ile Pro Gly Val Tyr Ser Gly Gly Ser
                20                  25                  30

Trp Glu Thr Ala His Ala Thr Phe Tyr Gly Gly Ser Asp Ala Ser Gly
            35                  40                  45

Thr Met Gly Gly Ala Cys Gly Tyr Gly Asn Leu Tyr Ser Gln Gly Tyr
        50                  55                  60

Gly Val Asn Thr Ala Ala Leu Ser Thr Ala Leu Phe Asn Asn Gly Leu
65                  70                  75                  80

Ser Cys Gly Ala Cys Phe Glu Leu Lys Cys Thr Asn Thr Pro Asn Trp
                85                  90                  95

Lys Trp Cys Leu Pro Gly Asn Pro Ser Ile Leu Ile Thr Ala Thr Asn
                100                 105                 110

Phe Cys Pro Pro Asn Tyr Ala Leu Pro Asn Asp Asn Gly Gly Trp Cys
            115                 120                 125

Asn Pro Pro Arg Pro His Phe Asp Leu Ala Met Pro Met Phe Leu Lys
        130                 135                 140

Leu Ala Gln Tyr Arg Ala Gly Ile Val Pro Val Thr Tyr Arg Arg Ile
145                 150                 155                 160

Pro Cys Arg Lys Gln Gly Gly Ile Arg Phe Thr Ile Asn Gly Phe Arg
```

```
                             165                 170                 175
        Tyr Phe Asn Leu Val Leu Ile Thr Asn Val Ala Gly Ala Gly Asp Ile
                    180                 185                 190

Ile Lys Val Trp Val Lys Gly Thr Lys Thr Asn Trp Ile Pro Leu Ser
                195                 200                 205

Arg Asn Trp Gly Gln Asn Trp Gln Ser Asn Ala Val Leu Thr Gly Gln
            210                 215                 220

Ser

225
```

(2) INFORMATION FOR SEQ ID NO:3:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..501
        (D) OTHER INFORMATION: /product= "strawberry FaEx1"

(xi) SEQUENCE DESCRIPTION: SEQ ID NO:3:

```
GGA ACC ATG GGG GGT GCT TGT GGA TAT GGA AAC CTC TAC AGC CAG GGC       48
Gly Thr Met Gly Gly Ala Cys Gly Tyr Gly Asn Leu Tyr Ser Gln Gly
 1               5                  10                  15

TAC GGA GTC AAC ACT GCT GCG CTG AGC ACG GCT CTG TTC AAC AAT GGC       96
Tyr Gly Val Asn Thr Ala Ala Leu Ser Thr Ala Leu Phe Asn Asn Gly
                20                  25                  30

CTG AGC TGC GGC GCT TGC TTC GAG ATC AAG TGC GGC GAC GAC CCA AGG      144
Leu Ser Cys Gly Ala Cys Phe Glu Ile Lys Cys Gly Asp Asp Pro Arg
            35                  40                  45

TGG TGC ACT GCC GGA AAG CCC TCC ATT TTC GTC ACC GCC ACC AAC TTC      192
Trp Cys Thr Ala Gly Lys Pro Ser Ile Phe Val Thr Ala Thr Asn Phe
        50                  55                  60

TGC CCT CCC AAC TTC GCT CAG CCC AGC GAC AAT GGC GGT TGG TGC AAC      240
Cys Pro Pro Asn Phe Ala Gln Pro Ser Asp Asn Gly Gly Trp Cys Asn
 65                 70                  75                  80

CCT CCC CGG ACC CAC TTG GAC CTT CGC CAT GCC CAT GTT CTC AAG ATC      288
Pro Pro Arg Thr His Leu Asp Leu Arg His Ala His Val Leu Lys Ile
                85                  90                  95

GCC GAG TAC AAA GCC GGA ATC GTC CCC GTC TCT TAC CGC GGT GTC CCA      336
Ala Glu Tyr Lys Ala Gly Ile Val Pro Val Ser Tyr Arg Arg Val Pro
            100                 105                 110

TGC GTA AAG AAG GGT GGG ATC AGG TTC ACA ATC AAC GGC CAC AAG TAC      384
Cys Val Lys Lys Gly Gly Ile Arg Phe Thr Ile Asn Gly His Lys Tyr
        115                 120                 125

TTC AAC CTG GTT CTG ATC ACC AAC GTG GCG GGC GCA GGG GAT ATC GTG      432
Phe Asn Leu Val Leu Ile Thr Asn Val Ala Gly Ala Gly Asp Ile Val
130                 135                 140

AGC GTG AGC GTG AAA GGC ACC AAC ACC GGG TGG ATG CCA ATG AGC CGA      480
Ser Val Ser Val Lys Gly Thr Asn Thr Gly Trp Met Pro Met Ser Arg
145                 150                 155                 160

AAT TGG GGT CAA AAC TGG CAG                                          501
Asn Trp Gly Gln Asn Trp Gln
                165
```

(2) INFORMATION FOR SEQ ID NO:4:

(i) SEQUENCE CHARACTERISTICS:
       (A) LENGTH: 167 amino acids
       (B) TYPE: amino acid
       (D) TOPOLOGY: linear (ii) MOLECULE TYPE: protein (xi) SEQUENCE DESCRIPTION: SEQ ID NO:4:

Gly Thr Met Gly Gly Ala Cys Gly Tyr Gly Asn Leu Tyr Ser Gln Gly
 1               5                  10                  15

Tyr Gly Val Asn Thr Ala Ala Leu Ser Thr Ala Leu Phe Asn Asn Gly
            20                  25                  30

Leu Ser Cys Gly Ala Cys Phe Glu Ile Lys Cys Gly Asp Asp Pro Arg
        35                  40                  45

Trp Cys Thr Ala Gly Lys Pro Ser Ile Phe Val Thr Ala Thr Asn Phe
 50                  55                  60

Cys Pro Pro Asn Phe Ala Gln Pro Ser Asp Asn Gly Gly Trp Cys Asn
 65                  70                  75                  80

Pro Pro Arg Thr His Leu Asp Leu Arg His Ala His Val Leu Lys Ile
                85                  90                  95

Ala Glu Tyr Lys Ala Gly Ile Val Pro Val Ser Tyr Arg Arg Val Pro
            100                 105                 110

Cys Val Lys Lys Gly Gly Ile Arg Phe Thr Ile Asn Gly His Lys Tyr
        115                 120                 125

Phe Asn Leu Val Leu Ile Thr Asn Val Ala Gly Ala Gly Asp Ile Val
130                 135                 140

Ser Val Ser Val Lys Gly Thr Asn Thr Gly Trp Met Pro Met Ser Arg
145                 150                 155                 160

Asn Trp Gly Gln Asn Trp Gln
                165

(2) INFORMATION FOR SEQ ID NO:5:

(i) SEQUENCE CHARACTERISTICS:
       (A) LENGTH: 537 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..537
       (D) OTHER INFORMATION: /product= "melon CmEx1"

(xi) SEQUENCE DESCRIPTION: SEQ ID NO:5:

TGG GAC GCC ACG TTT TAT GGA GGC AGC GAT GCT TCC GGA ACC ATG GGT        48
Trp Asp Ala Thr Phe Tyr Gly Gly Ser Asp Ala Ser Gly Thr Met Gly
 1               5                  10                  15

GGT GCT TGT GGG TAT GGC AAT CTC TAC AGC CAG GGC TAT GGC GTC AAC        96
Gly Ala Cys Gly Tyr Gly Asn Leu Tyr Ser Gln Gly Tyr Gly Val Asn
            20                  25                  30

ACA GCT GCT CTT AGT ACT GCT TTC TTC AAC AAT GGC CTC AGC TGT GGT       144
Thr Ala Ala Leu Ser Thr Ala Phe Phe Asn Asn Gly Leu Ser Cys Gly
        35                  40                  45

GCT TGC TTT GAG ATC AAG TGT GCT AAT GAC CCT CGA TGG TGC CAT CCT       192
Ala Cys Phe Glu Ile Lys Cys Ala Asn Asp Pro Arg Trp Cys His Pro
 50                  55                  60

GGT AGC CCT TGT ATC TTC ATT ACC GCT ACC AAT TTT TGT CCC CCT AAC       240
Gly Ser Pro Cys Ile Phe Ile Thr Ala Thr Asn Phe Cys Pro Pro Asn
 65                  70                  75                  80

-continued

```
TTT GCT CTT CCT AAT GAC AAT GGC GGT TGG TGT AAC CTT CCT CGC ACT       288
Phe Ala Leu Pro Asn Asp Asn Gly Gly Trp Cys Asn Leu Pro Arg Thr
                85                  90                  95

CAT TTC GAC CTC GCT ATG CCT ATG TTC CTC AAG ATC GCT GAG TAC CGC       336
His Phe Asp Leu Ala Met Pro Met Phe Leu Lys Ile Ala Glu Tyr Arg
            100                 105                 110

GCT GGA ATC GGA CCT GTC TCT TAC CGC CGG GTT CCA TGT AGG AAA CAA       384
Ala Gly Ile Gly Pro Val Ser Tyr Arg Arg Val Pro Cys Arg Lys Gln
        115                 120                 125

GGA GGA ATC AGG TTC ACA ATC AAC GGT TTC CGT TAC TTC AAT TTG GTG       432
Gly Gly Ile Arg Phe Thr Ile Asn Gly Phe Arg Tyr Phe Asn Leu Val
    130                 135                 140

TTA ATC ACC AAC GTC GCG GGT GCA GGG GAT ATC GTG AGG GTC AGC GTA       480
Leu Ile Thr Asn Val Ala Gly Ala Gly Asp Ile Val Arg Val Ser Val
145                 150                 155                 160

AAA GGA TCA AAC ACC GGT TGG ATG AGC ATG AGT CGT AAT TGG GGC CAA       528
Lys Gly Ser Asn Thr Gly Trp Met Ser Met Ser Arg Asn Trp Gly Gln
                165                 170                 175

AAC TGG CAG                                                           537
Asn Trp Gln
```

(2) INFORMATION FOR SEQ ID NO:6:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:6:

```
Trp Asp Ala Thr Phe Tyr Gly Gly Ser Asp Ala Ser Gly Thr Met Gly
 1               5                  10                  15

Gly Ala Cys Gly Tyr Gly Asn Leu Tyr Ser Gln Gly Tyr Gly Val Asn
                20                  25                  30

Thr Ala Ala Leu Ser Thr Ala Phe Phe Asn Asn Gly Leu Ser Cys Gly
            35                  40                  45

Ala Cys Phe Glu Ile Lys Cys Ala Asn Asp Pro Arg Trp Cys His Pro
        50                  55                  60

Gly Ser Pro Cys Ile Phe Ile Thr Ala Thr Asn Phe Cys Pro Pro Asn
65                  70                  75                  80

Phe Ala Leu Pro Asn Asp Asn Gly Gly Trp Cys Asn Leu Pro Arg Thr
                85                  90                  95

His Phe Asp Leu Ala Met Pro Met Phe Leu Lys Ile Ala Glu Tyr Arg
            100                 105                 110

Ala Gly Ile Gly Pro Val Ser Tyr Arg Arg Val Pro Cys Arg Lys Gln
        115                 120                 125

Gly Gly Ile Arg Phe Thr Ile Asn Gly Phe Arg Tyr Phe Asn Leu Val
    130                 135                 140

Leu Ile Thr Asn Val Ala Gly Ala Gly Asp Ile Val Arg Val Ser Val
145                 150                 155                 160

Lys Gly Ser Asn Thr Gly Trp Met Ser Met Ser Arg Asn Trp Gly Gln
                165                 170                 175

Asn Trp Gln
```

(2) INFORMATION FOR SEQ ID NO:7:

(i) SEQUENCE CHARACTERISTICS:
        (A) LENGTH: 22 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:7:

GSNCAYGCNA CNTTYTAYGG NG                                             22

(2) INFORMATION FOR SEQ ID NO:8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

YTGCCARTTY TGNCCCCART T                                              21
```

FRUIT-SPECIFIC AND RIPENING-REGULATION EXPANSIN GENES TO CONTROL FRUIT TEXTURE AND SOFTENING

CROSS REFERENCE TO RELATED APPLICATIONS

Not applicable.

FEDERALLY SPONSORED RESEARCH OR DEVELOPMENT

Not applicable

BACKGROUND OF THE INVENTION

The primary cell wall of plants has been described as a network of cellulose microfibrils embedded in a hemicellulosic polysaccharide matrix, which interacts to some degree with an additional co-extensive matrix of pectin and other less abundant components including structural proteins (Carpita, N. C., et al., *Plant J*. 3:1 (1993)). In dicotyledons the predominant hemicellulose is xyloglucan and it has been suggested that cellulose microfibrils are coated and tethered by a framework of xyloglucan polymers (Hayashi, T., et al., *Plant Physiol*. 75:596 (1984); McCann, M. C., et al., *J. Cell Sci*. 96:323 (1990)). In a turgid cell, disassembly of this potentially load-bearing hemicellulose-cellulose network could provide a rate limiting step to cell wall expansion in elongation of cells, although an enzymic basis for wall loosening remains to be established.

In addition to elongation growth, disassembly of hemicellulose also appears to be integral to cell wall metabolism during fruit ripening in which cells typically undergo a complex change in textural and rheological characteristics. During ripening, both the pectic and hemicellulosic polymers generally undergo substantial depolymerization and solubilization (Gross, K. C., et al., *Plant Physiol*. 63:117 (1979); Huber, D. J., *Hortic. Rev*. 5:169 (1983)). Most of the research in the field has focused on pectin degradation, which results from the action of the ripening-related enzyme polygalacturonase (PG), as the key element underlying the softening process. Molecular genetic studies, however, have revealed that this process is not the primary determinant of fruit softening (Smith, C. J. S., et al., *Nature* 334:724 (1988); Giovannoni, J. J., et al., *Plant Cell* 1:53 (1989)), but may be a factor in other aspects of fruit quality (Schuch, W. et al, *HortScience* 26:1517 (1991)). Disassembly of the hemicellulose component of the wall during ripening is common to most fruit although the extent varies between species and most likely reflects the degradation of a mixture of polysaccharides by multiple enzymes. Candidates for mediating hemicellulose modification as a mechanism for cell expansion include endo-1,4-β-glucanases (EGases or "cellulases") (Fry, S. C., *Physiol. Plant*. 75:532 (1989)) and xyloglucan endotransglycosylases (XETs) (Fry, S. C., et al, *Biochem. J*. 282:821 (1992); Nishitani, K., et al, *J. Biol. Chem*. 267:21058 (1992)), which have both been associated with rapidly expanding tissues. Neither of these classes of enzymes, however, appears to cause extension of isolated cell walls in vitro (McQueen-Mason, S. J., et al., *Plant Cell* 4:1425 (1992)). Xyloglucan represents the predominant hemicellulose in many fruit including tomato, where degradation is apparent during ripening in wild fruit, but not in fruit of the rin (ripening inhibitor) tomato mutant which softens extremely slowly (Maclachlan, G., et al, *Plant Physiol*. 105:965 (1994)). Fruit ripening has been associated with both EGases (Lashbrook, C. C., et al.); Gonzalez-Bosch, C., et al, *Plant Physiol*. 111:1313 (1996)) and XETs (Maclachlan, G., et al., *Plant Physiol*. 105:965 (1994); Arrowsmith, D. A., et al., *Plant Mol. Biol*. 28:391 (1995)); however, the importance of these and other as yet uncharacterized enzymes in modifying hemicellulose abundance, distribution and interaction with other cell wall components in fruit have yet to be determined.

A class of proteins called expansins has recently been identified that cause cell wall loosening in stress-relaxation assays but which lack detectable hydrolytic or transglycosylase activity (McQueen-Mason, S. J., et al., (1992); McQueen-Mason, S. J., et al., *Planta* 190:327 (1993); McQueen-Mason, S. J., *Plant Physiol*. 107:87 (1995)). It has been proposed that expansins disrupt non-covalent linkages, such as hydrogen bonds, at the cellulose-hemicellulose interface, thereby loosening an important constraint to turgor-driven cell expansion (McQueen-Mason, S. J., (1995)).

Expansin gene families have been identified in cucumber, rice and Arabidopsis (Shcherban, T. Y., et al., *Proc. Natl. Acad. Sci. USA* 92:9245 (1995)) suggesting that divergent isoforms may act on different components of the cell wall, exhibit differential developmental and environmental regulation or tissue and cell-specific expression. Expansins, to date, have been examined only in vegetative tissues where the action of this class of proteins is to loosen cell walls. There has been no indication that expansins are expressed in fruits. The processes by which expansins contribute to the disassembly of cell walls is not known. Although significant progress has been made in the understanding of fruit ripening, new methods of controlling fruit ripening are needed. The present invention and adaptations of this invention addresses these needs.

SUMMARY OF THE INVENTION

The present invention is based, in part, on the isolation and characterization of expansin (Ex1) genes from fruits. The invention provides for isolated nucleic acid molecules comprising a tomato LeEx1 polynucleotide sequence, of about 900–1200 nucleotides and typically about 1100 nucleotides in length, which specifically hybridizes to SEQ ID NO:1 under stringent conditions. The LeEx1 polynucleotides of the invention encode a LeEx1 polypeptide of about 200–300 amino acids but more typically about 260 amino acids, as shown in SEQ ID NO:2. In addition, the invention encompasses isolated nucleic acid molecules comprising strawberry FaEx1 polynucleotide sequences, which specifically hybridize to SEQ ID NO:3 under stringent conditions. In addition to tomato- and strawberry-derived Ex1 polynucleotides and the polypeptides encoded by the polynucleotides, this invention encompasses isolated nucleic acid molecules comprising a CmEx1 polynucleotide sequence from melon, which specifically hybridizes to SEQ ID NO:5 under stringent conditions.

The nucleic acids of the invention may also comprise expression cassettes containing a plant promoter operably linked to an Ex1 polynucleotide. In some embodiments, the promoter is from a gene active in fruit. The Ex1 polynucleotide may be linked to the promoter in a sense or antisense orientation.

Methods of inhibiting Ex1 expression, and thus modifying cell walls in plant tissues and softening in fruit, in a plant are also provided. The methods comprise introducing into a plant an expression cassette containing a plant promoter operably linked to a Ex1 polynucleotide. The Ex1 may encode a Ex1 polypeptide or may be linked to the promoter in an antisense orientation. The expression cassette can be introduced into the plant by any number of means known in the art, including use of *Agrobacterium tumefaciens* vector or through sexual reproduction. An example of a polypeptide useful for this purpose is LeEx1 from tomato.

Methods of enhancing Ex1 expression, and thus modifying cell walls in plant tissues and softening in fruit, in a plant are also provided. The methods comprise introducing into a plant an expression cassette containing a plant promoter operably linked to a Ex1 polynucleotide. The Ex1 may encode a Ex1 polypeptide. The expression cassette can be introduced into the plant by any number of means known in the art, including use of *Agrobacterium tumefaciens* vector or through sexual reproduction.

The promoters of the invention can be used in methods of targeting expression of a desired polynucleotide to fruits or other organs of a plant. The methods comprise introducing into a plant an expression cassette containing a tissue-specific, for example, a fruit ripening-specific, promoter operably linked to a Ex1 polynucleotide sequence.

The invention also provides for transgenic plants comprising an expression cassette containing a plant promoter operably linked to an Ex1 polynucleotide. The Ex1 may encode a Ex1 polypeptide or may be linked to the promoter in an antisense orientation. The plant promoter may be from any number of sources, including a gene typically active in the cells of the fruit of a plant. The transgenic plant can be any desired plant but is often a member of the genera Lycopersicon, Fragaria or Cucumis.

DEFINITIONS

Figure 1:
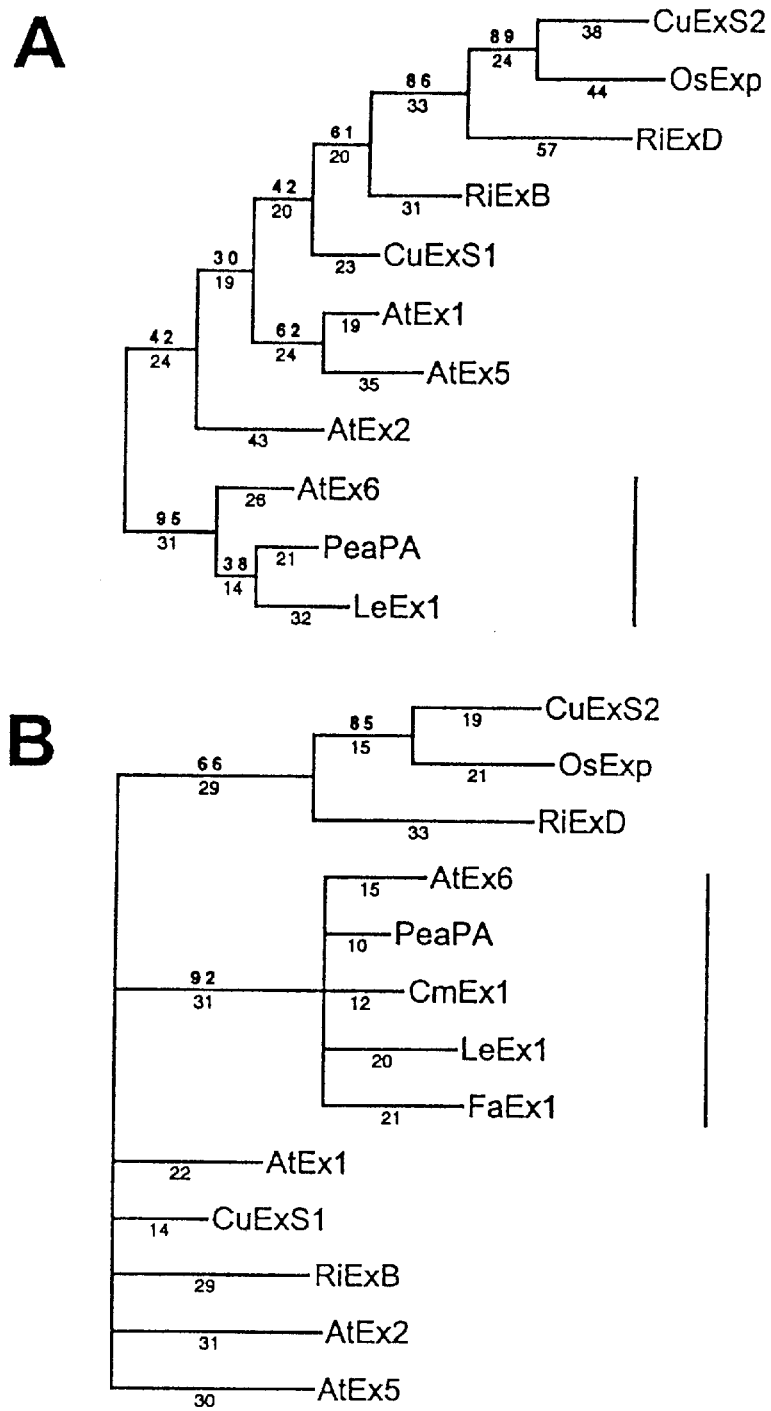
FIGS. 1A–1B shows (A) a phylogenetic tree of full length deduced amino acid sequences of 11 expansin homologs. CuExS1, CuExS2 (*Cucurnis sativus*); RiExB, RiExD (*Oryza sativa*); AtEx1, AtEx2, AtEx5, AtEx6 (*Arabidopsis thaliana*); PeaPA, (*Pisum sativum*) all identified in Shcherban, et al., (1995); OsExp (*Oryza saliva*) EMBL accession Y07782. (B) A similar alignment using truncated sequences of the above genes with deduced amino acid sequences of the PCR clones CmEx1 (*Cucumis melo*) and FaEx1 (*Fragaria ananassa*) derived from melon and strawberry fruit, respectively. For each alignment, bootstrap analysis used random stepwise addition of taxa with 100 replicates and global (tree bisection and reconnection) branch swapping. Bootstrap confidence values and branch lengths are depicted above and below the lines, respectively. A vertical line represents the position of the expansin sub-family containing three ripening-related genes (LeEx1, CmEx1 and FaEx1).

The term "antisense" refers to sequences of nucleic acids that are complementary to the coding mRNA nucleic acid sequence of a target gene. A DNA sequence linked to a promoter in an "antisense orientation" is linked to the promoter such that an RNA molecule complementary to the coding mRNA of the target gene is produced.

The term "exogenous to the plant" refers to a compound (typically a polynucleotide) which is introduced into the plant by any means other than by sexual reproduction. Examples of means by which this can be accomplished are described below, and include Agrobacterium-mediated transformation, biolistic methods, electroporation, in planta techniques, and the like. Such a plant containing the exogenous nucleic acid is referred to here as an $R_1$ generation transgenic plant. Transgenic plants which arise from sexual cross or by selfing are descendants of such a plant.

The term "expression cassette" refers to a polynucleotide sequence that comprises the coding sequence of interest and regulatory elements which affect expression of the protein of interest. Typically, expression cassettes include a promoter, the coding sequence of interest, a termination sequence, and a polyadenylation sequence. Optionally, expression cassettes can include enhancer elements and other regulatory elements.

The term "isolated nucleic acid" refers to a nucleic acid which is essentially free of other cellular components with which it is associated in the natural state. It is preferably in a homogeneous state although it can be in either a dry or aqueous solution. Purity and homogeneity are typically determined using analytical chemistry techniques such as gel electrophoresis or high performance liquid chromatography. In particular, an isolated Ex1 gene is separated from open reading frames which flank the gene and encode a protein other than Ex1. The term "purified" denotes that a nucleic acid gives rise to essentially one band in an electrophoretic gel. Particularly, it means that the nucleic acid is at least 85% pure, more preferably at least 95% pure, and most preferably at least 99% pure.

The term "modifying softness" refers to changing a plant's ripening sequence such that as fruit becomes ripe, it does not soften at the same rate as it would under natural conditions. Typically, softness is modified by changes in the structure of the cell walls of fruit.

The term "modifying or modification of cell walls" refers to changing the components, ratio of the components or structure of the components present in the cell walls of fruits, e.g., interference with the covalent interactions between cellulose microfibrils and matrix polysaccharides (McQueen-Mason, S. J. and Cosgrove, D. J. *Plant Physiol.* 107:87 (1995).

The term "operably linked" refers to functional linkage between a promoter and a second sequence, wherein the promoter sequence initiates transcription of RNA corresponding to the second sequence.

The term "polynucleotide," "polynucleotide sequence" or "nucleic acid sequence" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular Ex1 nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene. Ex1 polynucleotides, in general, can also be identified by their ability to hybridize under low stringency conditions (e.g., $T_m$–40° C.) to nucleic acid probes having a sequence of 8 to 300 bases, preferably a sequence of 80 to 100 bases in SEQ ID NO:1. An "LeEx1 polynucleotide" is a nucleic acid sequence comprising (or consisting of) a coding region of about 900 to about 1200 nucleotides, sometimes about 1100 nucleotides, which hybridizes to SEQ ID NO:1 under stringent conditions (as defined below), or which encodes a LeEx1 polypeptide.

The term "promoter" refers to a nucleic acid sequence that directs expression of a coding sequence. A promoter can be constitutive, i.e., relatively independent of the stage of differentiation of the cell in which it is contained or it can be inducible, i.e., induced be specific environmental factors, such as the length of the day, the temperature, etc. or a promoter can be tissue-specific, i.e., directing the expression of the coding sequence in cells of a certain tissue type.

The term "sense" refers to sequences of nucleic acids that are in the same orientation as the coding mRNA nucleic acid sequence. A DNA sequence linked to a promoter in a "sense orientation" is linked such that an RNA molecule which contains sequences identical to an mRNA is transcribed. The produced RNA molecule, however, need not be transcribed into a functional protein. As used here, an mRNA is an RNA molecule which is translated by ribosomes into polypeptides The term "sexual reproduction" refers to the fusion of gametes to produce seed by pollination. A "sexual cross" is pollination of one plant by another. "Selfing" is the production of seed by self-pollinization, i.e., pollen and ovule are from the same plant.

The term "specifically hybridizes" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), Vols. 1–3, Cold Spring Harbor Laboratory, (1989) ("Sambrook") or CURRENT PROTOCOLS IN MOLECULAR BIOLOGY, F. Ausubel et al., ed. Greene Publishing and Wiley-Interscience, New York (1987) ("Ausubel").

The term "stringent conditions" in the context of nucleic acid hybridization experiments such as Southern and northern hybridizations refers to sequence dependent, binding and washing environments. An extensive guide to the hybridization of nucleic acids is found in Tijssen (1993) LABORATORY TECHNIQUES IN BIOCHEMISTRY AND MOLECULAR BIOLOGY—HYBRIDIZATION WITH NUCLEIC ACID PROBES part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formalin with 1 mg of heparin at between 40 and 50° C., preferably 42° C., with the hybridization being carried out overnight. An example of highly stringent wash conditions is 0.15 M NaCl at from 70 to 80° C. with 72° C. being preferable for about 15 minutes. An example of stringent wash conditions is a 0.2× SSC wash at about 60 to 70° C., preferably 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1× SSC at 40 to 50° C., preferably 45° C. for 15 minutes. An example low stringency wash for a duplex of, e.g., more than 100 nucleotides, is 4–6× SSC at 35 to 45° C., with 40° C. being preferable, for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "transgenic plant" refers to a plant into which exogenous polynucleotides have been introduced by any means other than sexual cross or selfing. Examples of means by which this can be accomplished are described below, and include Agrobacterium-mediated transformation, biolistic methods, electroporation, in planta techniques, and the like. Such a plant containing the exogenous polynucleotides is referred to here as an $R_1$ generation transgenic plant. Transgenic plants may also arise from sexual cross or by selfing of transgenic plants into which exogenous polynucleotides have been introduced.

DETAILED DESCRIPTION OF THE INVENTION

The present invention provides for an expansin gene referred to as Ex1. Preferably the gene is isolated from tomato, melon and strawberry cDNA libraries, Also provided for in this invention, the claimed nucleic acid sequence can be used to suppress the expression of endogenous expansin in any fruit or other organs, thus modifying the structure of the cell walls of the fruit or plant and providing for ripe yet firm fruit and vegetables. As well as sense suppression of expansin in fruits, antisense mRNA and ribozymes can be used to suppress expansin.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook, et al.

A. Isolation of Nucleic Acid Sequences from Plants

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR®) technology to amplify the sequences of the genes directly from mRNA, from cDNA, from genomic libraries or cDNA libraries. PCR® and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying expansin-specific genes from plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Appropriate primers for this invention include, for instance: a 5' PCR primer [5'-G(GC)(N)CA(TC)GC(N)AC(N)TT(CT)TA(CT)GG(N)G-3'] (SEQ ID NO:7) and a 3' PCR primer [5'-(TC)TGCCA(AG)TT(TC)TG(N)CCCCA(AG)TT-3'] (SEQ ID NO:8) where N denotes all nucleotides. The amplifications conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Polynucleotides may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

B. Use of Nucleic Acids of the Invention to Inhibit Gene Expression

The isolated sequences prepared as described herein, can be used to prepare expression cassettes useful in a number of techniques. For example, expression cassettes of the invention can be used to suppress endogenous Ex1 gene expression. Inhibiting expression can be useful, for instance, in suppressing the extension of plant cell walls and disassembly of cell wall components.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy, et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of Ex1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff, et al., *Nature* 334:585–591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli, et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

C. Use of Nucleic Acids of the Invention to Enhance Gene Expression

In addition to inhibiting the process of softening in fruit, the polynucleotides of the invention can be used to accelerate the disassembly of cell walls. This can be accomplished by the overexpression of expansin.

The exogenous Ex1 polynucleotides do not have to code for exact copies of the endogenous Ex1 proteins. Modified Ex1 protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et aL, *Meth. Enzymol.* 194: 302–318 (1991)). For example, the chains can vary from the naturally occurring sequence at the primary structure level by amino acid substitutions, additions, deletions, and the like. These modifications can be used in a number of combinations to produce the final modified protein chain.

D. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence coding for the desired polypeptide, for example a cDNA sequence encoding the full length Ex1 protein, will preferably be combined with transcriptional and translational initiation regulatory sequences which will direct the transcription of the sequence from the gene in the intended tissues of the transgenic plant.

Promoters can be identified by analyzing the 5' sequences of a genomic clone corresponding to the expansin-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., *EMBO J.* 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. The tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

E. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *Embo J.* 3:2717–2722 (1984). Electroporation techniques are described in From, et al., *Proc. Natl. Acad. Sci. USA* 82:5824

(1985). Ballistic transformation techniques are described in Klein, et al., *Nature* 327:70–73 (1987).

*Agrobacterium tumefaciens*-mediated transformation techniques, including disarming and use of binary vectors, are well described in the scientific literature. See, for example Horsch, et al., *Science* 233:496–498 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype such as increased firmness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, 1983; and Binding, *REGENERATION OF PLANTS, PLANT PROTOPLASTS*, pp. 21–73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467–486 (1987).

To determine the presence of a reduction or increase of Ex1 activity, an enzymatic assay can be used. One of skill will recognize there are many different types of enzymatic assays that can be used, depending on the substrate used and the method of detecting the increase or decrease of a reaction product or by-product.

One of skill will recognize that other assays can be used to detect the presence or absence of Ex1. These assays include but are not limited to; immunoassays, electrophoretic detection assays (either with staining or western blotting), and complex carbohydrate (xyloglucan) detection assays.

The nucleic acids of the invention can be used to confer desired traits on essentially any plant. Thus, the invention has use over a broad range of plants, including species from the genera Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea. The Ex1 genes of the invention are particularly useful in the production of transgenic plants in the genera Lycopersicon, Fragaria and Cucumis.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Effects of gene manipulation using the methods of this invention can be observed by, for example, northern blots of the mRNA isolated from the tissues of interest. Typically, if the amount of mRNA has increased, it can be assumed that the endogenous Ex1 gene is being expressed at a greater rate than before. Other methods of measuring expansin activity can be used. For example, the firmness of fruits can be measured at specific times of ripening. This can be accomplished manually by gently squeezing the fruit or more quantitatively by measuring the viscosity of pureed fruit. The greater the viscosity, the greater the integrity of the cell walls and the firmer the fruit (see, e.g., U.S. Pat. No. 5,569,831). Because expansin affects the assembly of cell walls, an assay that measures the strength of cell walls, for example, stress relaxation assays, can also give a quantitative measure of expansin levels. Finally, levels of expansin expressed can be measured immunochemically, i.e., ELISA, RIA, EIA and other antibody based assays well known to those of skill in the art.

EXAMPLES

The following examples are offered to illustrate, but not to limit the claimed invention.

Example 1

RNA Isolation and PCR Amplification of Ex1 from cDNA Libraries.

Fruit and vegetative tissues were harvested from field-grown (Davis, Calif.) tomatoes (*Lycopersicon esculentum* cv. T5) and used as the source material in FIG. 1. Transgenic tomatoes expressing an ACC synthase antisense gene (Oeller, P. W., et al., *Science* 254:437 (1991)) were greenhouse-grown (Davis, Calif.), and fruit used as a source of RNA for northern blots. *Lycopersicon esculentum* cv Ailsa Craig were grown as described in Carpita, N. C., et al., *Plant J.* 3:1 (1993)). In all cases, plant tissues were harvested at the indicated times and stages, immediately frozen in liquid nitrogen and stored at −80° C.

Total RNA was extracted from frozen tomato pericarp and vegetative tissues as in Rose, J. K. C., et al., *Plant Physiol.* 110:493 (1996) and additional nucleic acid techniques used were as described in Sambrook, et al. unless specified otherwise.

An alignment of deduced amino acid sequences from nine expansins (Shcherban, T. Y., et al. (1995)) was used to identify two conserved amino acid domains for the construction of degenerate PCR primers. The 5' primer, (G(GC)(N)CA(TC)GC(N)AC(N)TT(CT)TA(CT)GG(N)G) (SEQ ID No:7) corresponded to amino acids 6–11 of the consensus sequence and the 3' primer ((TC)TGCCA(AG)TT(TC)TG(N)CCCCA(AG)TT) (SEQ ID NO:8) to amino acids 182–188 (N=all four nucleotides). cDNA was synthesized from 6 μg of turning (not yet pink) fruit total RNA and the cDNA amplified by PCR® with 0.5 μg cDNA for 40 cycles (94° C. for 1 min, 50° C. for 1.5 min and 72° C. for 1.5 min) as described in Rose, et al (1996). The resulting 542 bp cDNA fragment was gel-purified and cloned into pCR-II® (Invitrogen, San Diego, Calif.). The DNA sequence was determined with universal and specific internal primers (Genset Corporation, La Jolla, Calif.), using an ABI 377® (Perkin-Elmer) utilizing dye terminator chemistry with AmpliTaq® DNA polymerase and fluorescein (Perkin-Elmer/Applied Biosystems Division [PE/ABI], Foster City, Calif.). The PCR® fragment (probe 1) was radiolabeled by random priming with [α-$^{32}$P]dATP (3000 Ci/mmol, DuPontNEN, Boston, Mass.) by Klenow DNA polymerase (USB, Cleveland, Ohio).

The probe was used to screen a red ripe fruit cDNA library in the pARC7 vector (DellaPenna, D., et al., *Proc. Natl. Acad. Sci. USA* 83:6420 (1986)). Eight independent inserts were subcloned from the library vector into the XbaI site of the pBluescript II® SK+ plasmid (Stratagene Inc., La Jolla, Calif.) and sequenced for the PCR® product. The longest clone was designated LeEx1.

Similar reverse transcriptase-PCR® (RT-PCR®) reactions to those described above were carried out using RNA from ripening melon and strawberry fruit.

Example 2
Cloning and Phylogenetic Analysis of Ex1.

Sequence analysis of a 542 bp cDNA fragment derived by RT-PCR from turning tomato fruit RNA indicated the existence of an expansin homolog in tomato fruit (LeEx1). Subsequent screening of a red ripe tomato fruit cDNA library identified thirty positives clones, eight of which were selected based on size, subcloned and confirmed to have an identical sequence to the original LeEx1 partial-length cDNA and to each other, but of different lengths. The longest clone (1070 bp) encoded a predicted polypeptide of 261 amino acids with a $NH_2$-terminal signal sequence of 30 amino acids when the (−3,−1) rule was applied (von Heijne, G., *Nucleic Acids Res.* 14:4683 (1986)). An ATG codon initiated an open reading frame at position 28 and a TAA consensus stop codon was present at position 811.

A search of the GenBank database with the LeEx1 deduced amino acid sequence revealed a high degree of homology to two biochemically characterized expansins from cucumber (Shcherban, T. Y., et a. (1995)) and homologs from Arabidopsis, rice and pea. Previous analyses of these sequences identified no known functional motifs. However, it has been suggested that the N-termini contain 8 conserved cysteines have similar spacing to the chitin-binding domain of wheat-germ agglutinin, and the C-termini contain a region of conserved tryptophan residues somewhat similar to the cellulose binding domain of bacterial cellulases (Shcherban, T. Y., et al. (1995)). The LeEx1 deduced amino acid sequence was aligned with five sequences from four other species, comprising both monocotyledons and dicotyledons and conservation of these features at the N- and C-termini was observed. Amino acid identity was apparent throughout the proposed mature polypeptides with substantial sequence divergence being evident over approximately the first thirty amino acids, corresponding to the predicted signal sequences. The sequence identity over the entire coding sequence between LeEx1 and two cucumber expansins (CuExS1, 66%; CuExS2, 58%), a pea pollen allergen (PeaPA, 78%), and sequences from Arabidopsis (AtEx6, 76%) and rice (OsExp, 56%) is of the same degree as that between the two biochemically characterized cucumber expansins (63% over the same region), suggesting that all these genes encode expansins.

The above sequences and six additional homologous genes, comprising full-length sequences from rice and Arabidopsis, were aligned using Pileup® Vers. 8 (Wisconsin Package, Genetics Computer Group, Madison, Wis.). A phylogram was derived (FIG. 1A) with a pollen allergen from *Phleum pratense* (GenBank accession number X78813) as the outgroup, using PAUP software (Swofford, D., *Illinois Natural History Survey* Champaign, Ill. (1993)) and bootstrap analysis. PhP1 is somewhat divergent from the other sequences (approximately 25% sequence identity); however, it retains some regions of higher homology as well as the conserved tryptophans described above, and it has been suggested that this class of allergens may function as expansins (Cosgrove, D. J., *BioEssays* 18:533 (1996)). LeEx1 aligned in a distinct clade with PeaPA, a sequence originally described as a pollen allergen and tEx6 from Arabidopsis, neither of which have been studied in terms of their expression patterns or biochemical properties. Other Arabidopsis sequences aligned with different branches and, as has been noted previously (Shcherban, T. Y., et al. (1995)), appear to be more related to other sequences from both monocotyledons and dicotyledons suggesting that divergence of these genes predated the evolutionary divergence of the angiosperms.

Similar RT-PCR® reactions were carried out using RNA from ripening melon and strawberry fruit and in each case cDNAs (CmEx1 and FaEx1, respectively) with high sequence similarity to LeEx1 were identified, suggesting that the expression of expansin genes may be a common feature of ripening fruit.

To determine whether ripening-associated expansins define a sub-family of expansin genes, each of the sequences in FIG. 1A was truncated to correspond to the size of the strawberry and melon PCR® fragments and aligned as described above (FIG. 1B). Alignment of this truncated domain demonstrated a phylogenetic relationship between all of the expansins similar to that observed over the entire sequence (FIG. 1A) and furthermore indicated that along with PeaPA and AtEx6, the ripening associated expansins define a sub-family of expansin genes.

Example 3
Detection of Ex1 DNA and RNA from Tomato Tissues.

Figure 2:
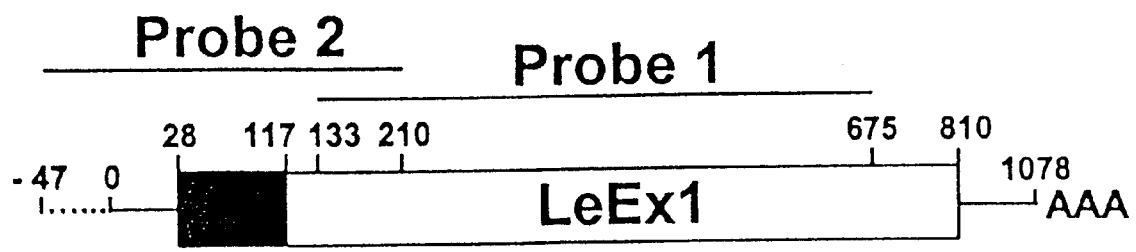
FIG. 2 is a diagram of the LeEx1 gene and 47 bp of 5' flanking sequence derived from the pARC7 and pBluescript® II cloning vectors. The boxed region represents the coding sequence with the filled area comprising the putative signal sequence. Both 5' and 3' untranslated regions are depicted by unbroken lines and residual cloning vector sequence by a broken line. Nucleotide numbers are indicated above the gene. Two probes were designed from this sequence and used for northern and Southern analyses. Probe 1 corresponded to a more conserved sequence among expansins while probe 2 corresponded to more divergent sequence.

Expansin gene families of varying complexity have been reported in Arabidopsis, rice and cucumber (Shcherban, T. Y., et al. (1995); Cosgrove, D. J. (1996)). FIG. 2 represents the LeEx1 cDNA clone and indicates the regions of the cDNA used to construct two probes for the determination of the potential complexity of the expansin gene family in tomato. Probe 1 (amino acids 133–675) corresponded to the central portion of the gene that is most conserved among the expansins and their homologs (FIG. 1).

A. Southern Blot Analysis.

Genomic DNA was isolated from young tomato leaves (cv T5) as in Sambrook, et al 20 μg aliquots were digested with Hind III, NcoI, XbaI and DraI, fractionated on a 0.8% (w/v) agarose gel. The contents of the gel were transferred to Hybond-N® membrane (Amersham, Arlington Heights, Ill.). The blot was hybridized with probe 1 as described above. Hybridization and washing procedures were as described in Rose, et al. (1996) but the final three washes were at 45° C. ($T_m$−33° C.). Probe 1 was removed from the blot with three washes of 0.1% SDS at 65° C. and re-probed with a 257 bp radiolabeled fragment (probe 2) corresponding to nucleotides 1–210 of LeEx1 plus nucleotides 814–850 of the pARC7 and 736–745 of the pBluescript II® plasmids. Hybridization was performed as before but the final three washes were at 60° C. ($T_m$−18° C.).

B. Northern Blot Analysis.

Total RNA was isolated from all tissues as described above and 15 μg from each sample subjected to electrophoresis on 1.2% agarose (w/v)/10% (v/v) formaldehyde denaturing gels and transferred to Hybond-N® membrane. The blot was prepared as described in Yen, H., el al., *Plant Physiol.* 107:1343 (1995)). Membranes hybridized with probe 2 were washed three times at 65° C. ($T_m$−18° C.). The membrane hybridized with probe 1 was washed at 45° C. ($T_m$−38° C.). Hybridization was quantified by exposure to a phosphorimager plate and analyzed with a Fujix BAS 1000® phosphorimager and Fujix MacBAS® software (Fuji Medical Systems, Stamford, Conn.).

C. Results.

A Southern blot of tomato genomic DNA hybridized with probe 1 and washed at low stringency revealed one major hybridizing band and at least two weaker bands, suggesting that LeEx1 is a member of small multi gene family. Since larger expansin gene families have been reported in other species (Cosgrove, D. J. (1996)), it is possible that only a subset of the total tomato expansin gene family was detected and that LeEx1 may reflect a divergent clade which does not cross-hybridize with other expansin genes (FIG. 2A). A second probe (probe 2) was designed from the more divergent 5' portion of LeEx1 and used to probe the same Southern blot. Only the single major band that was seen with probe 1 was evident, indicating that probe 2, when used at this stringency, detected a single gene in tomato.

Both probes were used to examine expression of LeEx1 and related genes in a variety of tomato tissues at the level of mRNA abundance, at the same relative stringencies as the Southern blots. Probe 1 hybridized strongly to a 1.1 kb RNA isolated from fruit at the turning stage of ripening. After prolonged exposure of the membrane to X-ray film, a low level of hybridization (<1% of signal in turning fruit) was detected with RNA in roots, hypocotyls, stems and young leaves. Interestingly, expression was not detected in anthers, which presumably contained a quantity of pollen, despite the homology of LeEx1 and other expansins to pollen allergens. Probe 2 detected a similar abundance of LeEx1 mRNA in turning fruit but not in other tissues, even after prolonged exposure of the blot to X-ray film, suggesting that the expression of LeEx1 is fruit specific.

Example 4
Ethylene Treatment of Tomatoes.

Fruit development from a mature ovule through final maturity encompasses a wide range of complex and highly regulated physiological processes. Early development in most fruit can be divided into three phases: fruit set, cell division and cell expansion (Gillaspy, G. H., et al. *Plant Cell* 5:1439 (1993)). Upon reaching full expansion ripening is initiated, typically involving changes in color, aroma, flavor and a textural transition that contributes to softening of the tissue. The ripening process in climacteric fruit such as tomato, banana and apple is highly regulated by the plant hormone ethylene which is thought to coordinate the numerous metabolic pathways necessary for normal ripening.

Expression of LeEx1 was examined at the level of mRNA in fruit ripened either attached to the vine, or harvested prior to the onset of ripening at the mature green stage and allowed to ripen off the vine, in the presence of air or exogenous ethylene.

Fruit were assigned a developmental stage based on size or color (Gonzalez-Bosch, C., et al.,(1996)). Pericarp tissue was isolated from young expanding fruit (stages I, II and III corresponding fruit diameters of 0.5–1 cm, 2–3 cm and 4–6 cm, respectively), vine-ripened or post-harvest treated fruit. Mature green (MG) fruit were determined by both color and ethylene production using a gas chromatograph fitted with a flame ionization detector. Fruit at the MG1 stage (0.02–0.1 nL ethylene $gf^{wt-1}$ $h^{-1}$) were used for subsequent continuous-flow experiments and treatments with the ethylene inhibitor 2, 4-norbornadiene (NBD; Aldrich Chemicals, Milwaukee, Wis.), which competes with ethylene for the ethylene receptor (Sisler, E. C., et al., *Phytochem.* 23:2765 (1984)). MG1 fruit were placed in 5 L containers and allowed to ripen in a continuous flow (20 L/hour) of humidified air or 10 μL/L ethylene at 25° C. Fruit were removed and flash frozen at the same defined stages of ripening as above. For NBD treatments, MG1 fruit were placed in sealed 20 L chambers and held in air, or with 2 mL NBD with or without 10 μL/L ethylene. Air-treated control fruit were allowed to ripen to the breaker+4 day or red ripe+4 day stages and on the same day the NBD-treated, or NBD plus ethylene-fruit was collected.

In vine-ripened fruit, LeEx1 was not detected in either expanding or full-size non-expanding fruit prior to the breaker stage, which marks the onset of autocatalytic ethylene production. LeEx1 mRNA was first detected at the breaker stage of fruit ripening and its abundance increased dramatically at the turning stage, remaining extremely high throughout ripening. Similar patterns of LeEx1 expression were evident in fruit ripened off the vine in the presence or absence of exogenous ethylene, suggesting that LeEx1 expression is tightly linked to ripening, since temporally the air-ripened fruit reached the same ripening stage as the ethylene-treated fruit 7–10 days later.

LeEx1 mRNA accumulation was abolished by NBD in fruit at breaker+4 day and showed several reduced levels in over-ripe fruit. This effect was reversed in both stages by co-incubation with ethylene, presumably due to competition for the ethylene receptor, suggesting that ethylene directly regulates LeEx1 mRNA abundance.

The autocatalytic nature of ethylene production during ripening complicates any determination of the threshold levels necessary to induce LeEx1 mRNA accumulation and the time frame in which induction occurs. These questions were addressed using transgenic tomatoes exhibiting a greater than 99% inhibition of ethylene production, resulting from the expression of an antisense RNA of ACC synthase (Oeller, P. W., et al. (1991)). Transgenic fruit from these plants fail to ripen in the absence of exogenous ethylene and six days of continuous treatment of mature green transgenic fruit with 10 μL/L ethylene are necessary to restore a normal phenotype (Theologis, A., *Cell* 70:181 (1992)).

Flowers of the ACC synthase antisense transgenic plants were tagged at anthesis and mature green fruit harvested 37 days after pollination. Fruit were placed in 20 L chambers and held in continuous flow (20 L/hour) of humidified air or a defined ethylene concentration at 25° C. for a period of up to 24 hours.

Expression of LeEx1 mRNA was examined in these fruit treated for 24 hours with a range of ethylene concentrations and over a time course of 24 hours with 10 μL/L ethylene. Basal levels of LeEx1 mRNA were detected prior to treatment. Following incubation for 24 hours in a range of ethylene concentrations, the threshold of ethylene induction was seen at 0.1–1 μL/L ethylene with little difference between 10 μL/L and 100 μL/L treatments. During a treatment of fruit with 10 μL/L exogenous ethylene over a 24 hour time course, a large induction of LeEx1 mRNA accumulation was seen after 6 hour and increased linearly throughout the 24 hour treatment, suggesting that LeEx1 mRNA is relatively stable or that the transcription rate also continued to increase over 24 hours. The rapid induction of LeEx1 mRNA following only 6 h of treatment with exogenous ethylene indicates that LeEx1 transcription or transcript stability is ethylene regulated.

An alternative approach to dissecting the complexity and molecular basis of the ripening process has been through the study of ripening mutations, principally in the pleiotropic tomato mutants Nr, never ripe; rin, ripening inhibitor and nor, non-ripening. Nr is a dominant mutation, resulting from a single amino acid change in a homolog of the Arabidopsis ethylene receptor ETR1 (Wilkinson, J. O., et al., *Science* 270:1807 (1995)). Fruit of the Nr mutant exhibit only partial, delayed ripening and minimal softening occurs. The bases for the rin and nor mutations, both of which are recessive, are not known; however, the ripening-impaired phenotypes are more severe (Tigchelaar, E. C., et al., *Hort-Science* 13:508 (1978)) and fruit softening is dramatically reduced (Mitcham, E. J., et al., *Phytochem.* 30:1777 (1978)). All three ripening-impaired mutants have been used as tools to study the processes underlying cell wall disassembly during fruit ripening, through analysis of the expression of cell wall hydrolases such as polygalacturonase (DellaPenna, D., et al., *Plant Physiol.* 85:502 (1987)) and endo-1,4-β-glucanases (Gonzalez-Bosch, C., et al. (1996)), and of cell wall polymer synthesis (Mitcham, E. J., (1991) and degradation (Maclachlan, G., et al. (1994)) during ripening. Following a similar approach, the accumulation of LeEx1 mRNA was examined in mature green, breaker, red ripe and ethylene-treated mature green wild type Ailsa Craig cultivar fruit, and equivalent-age Nr, rin and nor mutant fruit.

As before, high levels of LeEx1 mRNA were detected at the breaker and red ripe stages in wild type and abundance increased in mature green fruit upon ethylene treatment. In nor and rin fruit, basal levels of transcript (<1% and 2% of wild type, respectively) were detected and exogenous ethylene treatment of mature green fruit caused no detectable induction. High levels of LeEx1 mRNA were apparent in Nr, equivalent to those in wild type; however, ethylene treatment did not induce enhanced mRNA levels. The severity of the Nr phenotype appears to depend on the genetic background and the fruit of the Nr in the Ailsa Craig background, used in these experiments, exhibit a degree of ethylene responsiveness and ripen to a greater extent than in other backgrounds (Lanahan, M. B., et al., *Plant Cell* 6:521 (1994)). The possibility that high levels of LeEx1 mRNA accumulation were detected partly as a result of a leaky Nr mutation cannot be excluded.

It has been demonstrated that a variety of ripening-related genes are differentially expressed among these mutants and a model has been proposed in which the Nr gene product is necessary for regulation of most ethylene-regulated genes (Yen, H., et al., (1995)). These comprise genes which are regulated either primarily by ethylene or by an additional developmental component. The model further describes the rin and nor gene products as regulatory elements of a developmental pathway in which fruit acquire competence to respond to the ethylene signal, thereby playing a more indirect role in ethylene perception. The expression patterns of LeEx1 mRNA in these experiments taken together with the previous experiments suggest that LeEx1 is regulated directly by ethylene and is also influenced by a developmental pathway that appears to be modulated by the rin and nor genes. The severely reduced levels of detectable LeEx1 mRNA in the non-softening rin and nor mutants suggest that LeEx1 may play a role in the cell wall disassembly that occurs during fruit ripening.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid molecule comprising an LeEx1 polynucleotide which specifically hybridizes to SEQ ID NO:1 under stringent conditions.

2. The isolated nucleic acid molecule of claim 1, wherein the LeEx1 polynucleotide is between about 900–1200 nucleotides in length.

3. The isolated nucleic acid molecule of claim 2, wherein the polynucleotide is about 1100 nucleotides in length.

4. The isolated nucleic acid molecule of claim 1, wherein the LeEx1 polynucleotide is SEQ ID NO:1.

5. The isolated nucleic acid molecule of claim 1, wherein the LeEx1 polynucleotide encodes an expansin polypeptide of between about 200–300 amino acids.

6. The isolated nucleic acid molecule of claim 5, wherein the polynucleotide encodes an expansin polypeptide of about 260 amino acids.

7. The isolated nucleic acid molecule of claim 5, wherein the expansin polypeptide has an amino acid sequence as shown in SEQ ID NO:2.

8. The isolated nucleic acid molecule of claim 1, further comprising a plant promoter operably linked to the LeEx1 polynucleotide.

9. The isolated nucleic acid molecule of claim 8, wherein the LeEx1 polynucleotide is linked to the promoter in the antisense orientation.

10. An isolated nucleic acid molecule comprising a LeEx1 polynucleotide, said polynucleotide encoding an expansin polypeptide of between about 200–300 amino acids and having an amino acid sequence as shown in SEQ ID NO:2.

11. A method of modifying softness in fruits of a transgenic plant, the method comprising introducing into the plant an expression cassette comprising a promoter active in cells of fruits operably linked to an Ex1 polynucleotide which specifically hybridizes to SEQ ID NO:1 under stringent conditions.

12. The method of claim 11, wherein the Ex1 polynucleotide is LeEx1.

13. The method of claim 11, wherein the Ex1 polynucleotide is linked to the promoter in the antisense orientation.

14. The method of claim 11, wherein the Ex1 polynucleotide is exogenous to the plant.

15. The method of claim 11, wherein the introduction of Ex1 polynucleotide into a plant is by sexual reproduction.

16. The method of claim 11, wherein the promoter is derived from plants.

17. The method of claim 11, wherein the promoter is constitutive.

18. A method of modifying cell walls in the tissues of a transgenic plant, the method comprising introducing into the plant an expression cassette comprising a promoter operably linked to an Ex1 polynucleotide which specifically hybridizes to SEQ ID NO:1 under stringent conditions.

19. The method of claim 18, wherein the Ex1 polynucleotide is linked to the promoter in the antisense orientation.

20. The method of claim 18, wherein the Ex1 polynucleotide is exogenous to the plant.

21. The method of claim 18, wherein the introduction of Ex1 polynucleotide into a plant is by sexual reproduction.

22. The method of claim 18, wherein the promoter is derived from plants.

23. The method of claim 18, wherein the promoter is constitutive.

24. A transgenic plant comprising an expression cassette comprising a promoter operably linked to an Ex1 polynucleotide which specifically hybridizes to SEQ ID NO:1 under stringent conditions.

25. The transgenic plant of claim 24, wherein the Ex1 polynucleotide is operably linked to the promoter in the antisense orientation.

26. The transgenic plant of claim 24, wherein the promoter is derived from plants.

27. The transgenic plant of claim 24, wherein the promoter is constitutive.

28. The transgenic plant of claim 24, which is a member of the genus Lycopersicon.

29. The transgenic plant of claim 24, which is a member of the genus Fragaria.

30. The transgenic plant of claim 24, which is a member of the genus Cucumis.

* * * * *